United States Patent
Orthman (12) United States Patent (10) Patent No.: US 6,358,749 B1
(45) Date of Patent: Mar. 19, 2002

(54) AUTOMATED SYSTEM FOR CHROMOSOME MICRODISSECTION AND METHOD OF USING SAME

(75) Inventor: David W. Orthman, Denver, CO (US)

(73) Assignee: Ozo Diversified Automation, Inc., Denver, CO (US)

( * ) Notice: Subject to any disclaimer, the term of this patent is extended or adjusted under 35 U.S.C. 154(b) by 0 days.

(21) Appl. No.: 09/205,256

(22) Filed: Dec. 2, 1998

Related U.S. Application Data (60) Provisional application No. 60/067,227, filed on Dec. 2, 1997.

(51) Int. Cl.[7] ............................. G01N 1/04; G01N 1/08; C12N 1/08

(52) U.S. Cl. ...................... 436/177; 436/174; 359/368; 422/99; 422/101; 435/286.2; 435/309.1

(58) Field of Search ................................. 436/174, 177; 422/99, 101; 435/6, 270, 286.2, 287.3, 309.1; 359/368

(56) References Cited

U.S. PATENT DOCUMENTS

| | | |
|---|---|---|
| 4,601,551 A | 7/1986 | Pettingell et al. |
| 4,694,230 A | 9/1987 | Slocum et al. |
| 5,225,750 A | 7/1993 | Higuchi et al. |
| 5,326,691 A | 7/1994 | Hozier |
| 5,410,638 A | 4/1995 | Colgate et al. |
| 5,449,604 A | 9/1995 | Schellenberg et al. |
| 5,563,060 A | 10/1996 | Hozier |
| 5,568,004 A | 10/1996 | Kleindiek |
| 5,580,728 A | 12/1996 | Perlin |
| 5,658,730 A | 8/1997 | McGill et al. |
| 5,665,549 A | 9/1997 | Pinkel et al. |
| 5,670,320 A | 9/1997 | Wallace et al. |
| 5,671,086 A | 9/1997 | Parvin et al. |
| 5,843,644 A | 12/1998 | Liotta et al. |
| 5,843,657 A | 12/1998 | Liotta et al. |

FOREIGN PATENT DOCUMENTS

| | | |
|---|---|---|
| JP | 10-127267 | 5/1998 |

OTHER PUBLICATIONS

Ficher et al, J. Micormechanics and Microengineering, vol. 7, pp. 256–258, 1997.*

Kao, "Chromosome Microdissection and Microcloning: Application to Genome Analysis", Methods of Genome Analysis in Plants, pp. 329–343 (1996, CRC Press).

Kao et al. "Construction Characterization of Three Region–Specific Microdissection Libraries for Human Chromosome 18", Somatic Cell and Molecular Genetics, vol. 22, No. 3, 1996, pp. 191–199.

(List continued on next page.)

*Primary Examiner*—Jan Ludlow
(74) *Attorney, Agent, or Firm*—Sheridan Ross P.C.

(57) ABSTRACT

An automated system and method for chromosome microdissection involves securing a micro-tool, verifying a micro-tip position and configuration and execution of a predetermined cut pattern of a location identified by an equipment operator. The present method involves preparation of sample material on a slide placed upon a stage of an inverted optical microscope, location of the target sample for dissection, micro-tool calibration and microdissection itself. Micro-tool calibration involves the use of cameras, preferably mounted at an angle from each other, for seeing the micro-tool point, such cameras associated with vision software programs capable of locating the tool point tip at three-dimensional space. Microdissection is performed on an isolated section of chromosome placed within the appropriate three-dimensional stage. The present system and method provides reliability and ease of operation thus making microdissection widely available to laboratories.

2 Claims, 7 Drawing Sheets

OTHER PUBLICATIONS

Kao et al., "Complete SEt of Eleven Region–Specific Microdissection Libraries for Human Chromosome 2", Somatic Cell and Molecular Genetics, vol. 22, No. 1, 1996, pp. 57–66.

Kao et al., "Chromosome Microdissection and Cloning in Human Genome and Genetic Disease Analysis", Proc. Natl. Acad. Sci USA, vol. 88, pp. 1844–1848, Mar., 1991.

Yu et al., Construction and Characterization of a Region–Specific Microdissection Library from Human Chromosome 2q35–q37, Genomics 14, pp. 769–774 (1992).

Yu et al., "Gene Identification of DNA Sequence Analysis in the GC–Poor 20 Megabase Region of Human Chromosome 21", Proc. Natl. Acad. Sci USA, vol. 94, pp. 6862–6867, Jun., 1997.

"Analyzing Fixture Needs at the Design Process Stage or at the Start of the Job, and then Making the Fixture on the Router are the Steps to Efficient Depaneling", Electronic Manufacturing, Nov. 1998, pp. 21–22.

OZO Diversified Automation Brochure on PanelRouter Model 16SI, date unknown.

OZO Diversified Automation Brochure on Panelmaster 18HS, date unknown.

OZO Diversified Automation Sheet on Electronic Product Development System, date unknown.

OZO Diversified Automation Brochure on FixtureMaster Model 1071, date unknown.

OZO Diversified Automation, Inc. Sheet on OXO Benchtop Workstation and the Family of Interchangeable Tool Heads, date unknown.

* cited by examiner

AUTOMATED SYSTEM FOR CHROMOSOME MICRODISSECTION AND METHOD OF USING SAME

RELATED APPLICATION

This application claims priority from U.S. Provisional Patent Application No. 60/067,227, filed Dec. 2, 1997. The entire disclosure of the provisional application is considered to be part of the disclosure of the accompanying application and is hereby incorporated by reference.

FIELD OF THE INVENTION

The present invention is directed to an automated system for microdissection of a sample such as chromosomes or other biological material, and in particular, it relates to a robotic assisted microdissection system and method that significantly reduces the time and skill needed for cellular and sub-cellular dissections.

BACKGROUND OF THE INVENTION

Conventional surgical microdissection involves miniature tools performing cellular level dissection under a microscope. This can be an extremely tedious process. Miniature tools generally need to be fabricated in the laboratory by the researcher or technician using a micro-forge. The tools are then placed into the clamp of a micro-manipulator and moved about within the microscope's field of view. The micro-manipulator scales the operator's motion by some factor such as ten to one range. Even with the scaled movement of the micromanipulator, a great deal of practice and skill are needed to perform delicate operations such as chromosome dissection or in-vitro fertilization. Because microdissection is so physically demanding, it is a very low yield process (e.g., 4 per day), requiring frequent breaks from the work. In some situations large volumes of microdissected material are needed for significant (anywhere from 4 to 100) sampling to occur. For example, chromosome microdissection of a specific gene locus requires from 10 samples, up to 100 samples in order to gather enough material for subsequent processes. It can take up to a month for 100 microdissection samples to be taken. Manually positioning a micro-manipulator is a tedious process. A free standing micro-manipulator must be positioned by the operator sliding and bumping and tapping the base in an attempt to get the micro-tool point within the microscope's field of view. If a new micro tool is used after each operation, the sliding, bumping and tapping process must be repeated each time.

Prior to the use of PCR in micro cloning, the construction of microdissection libraries had several drawbacks; e.g. the size of each such library was generally small; e.g., such a library contained at most only a few hundred clones of the microdissected material. However, for a dissected region of 10–20 mb, many more micro clones may be required to adequately generate libraries of the dissected region. Furthermore, since unstained and unbanded chromosome preparations were preferably used in microdissection, the identification of individual chromosomes and the chromosome bands was difficult and less accurate. Although suitable translocation stocks in mouse or human/rodent cell hybrids could be used, the prospect of a wider application to many other genomes was severely curtailed. Finally, the need to dissect several hundred chromosome segments for micro cloning would discourage investigators to use microdissection as a general method.

Focused UV laser microbeams have been used in conjunction with microdissection (e.g. Ponelies et al., 1989). In this procedure, all unwanted nuclei and chromosome regions on the slide are destroyed by a laser beam, leaving only the needed region intact which is then picked up and transferred to an Eppendorf tube for PCR.

Various other micromanipulating devices are known that utilize various means for manipulating material. For example, Parvin et al., U.S. Pat. No. 5,671,086 uses electrophoresis wherein electrodes are coupled to the stage of a microscope in an array whereby the electrode array allows for distinct manipulations of the electric field for accurate manipulations of an object. Kleindiek, U.S. Pat. No. 5,568,004 utilizes an electromechanical positioning device that is moved for course and fine adjustment by the operator when viewing a subject through a microscope, preferably using a piezo-tube connected to variable voltages to cause movements of a tip means. Higuchi et al., U.S. Pat. No. 5,225,750 disclose a micro-injection apparatus utilizing a micromovement device which relies upon a piezo electric/electro strictive element, which, in response to an electrical signal, causes a micromovement of a microsyringe.

Currently, the major obstacle to more widespread adoption of surgical microdissection technology is the extreme difficulty of the actual chromosome microdissection itself. This procedure takes a very experienced and skilled cytogeneticist. It requires continuous practice and a very significant amount of training. Surgical microdissection is also slow compared to possible automated procedures. It requires extreme care with regard to contamination. Finally, the preparation of the micro-tools requires for the procedure is also currently imprecise and requires an experienced individual. Only a few laboratories have the necessary resources and demand for the technique to have established it themselves.

SUMMARY OF THE INVENTION

Molecular analysis and high resolution physical mapping of specific genomic regions in any organism require large numbers of probes from the region of interest. A direct approach is to use microdissection techniques to physically remove the critical region followed by a micro cloning procedure to construct a region-specific library. These region-specific libraries are useful in a wide variety of studies, particularly for high resolution genome analysis and to facilitate positional cloning of important disease genes mapped to a specific region. Some examples of applications include: (i) isolation of large insert clones, like Pl, for contig assembly to cover a given genomic region; (ii) isolation of highly poly-morphic markers for linkage analysis; (iii) isolation of large numbers of single-copy micro clones as STSs for high density coverage of the region, (iv) isolation of region-specific CDNA clones as candidate genes for positional cloning, and (v) serving as chromosome painting probes to analyze complex chromosomal abnormalities.

The present invention is directed to an automated system to carry out microdissection for use by scientists who are not well equipped in genome analysis but are anxious to clone disease genes as their primary interest. This system is useful in laboratories for production of both microdissection painting probes for specific regions of the human or any other genome, including the genomes of plants, mice, and other model organisms currently of interest, e.g., aradopsis and Rugu rubripes (the Japanese pufferfish). The reliability and ease of operation of the automated system makes it widely available to laboratories that occasionally need microdissection technology but are not in a position to establish the technology as it currently stands due to the extremely demanding technical aspects of the conventional procedure.

Before the completion of the sequencing project for the entire human genome, there will be continuing needs for region-specific libraries and clones in specific regions for contig construction, refined physical mapping, linkage analysis, candidate gene isolation, etc. , all of which are essential to a successful cloning of a critical disease gene.

The automated system of the present invention greatly simplifies other microdissection procedures, for example microdissection of tumor specimens to separate the tumor cells from the normal surrounding tissue, and in vitro fertilization. Therefore, the automated system described herein has wide biomedical application. The present invention provides a device and method that makes it possible to construct microdissection libraries efficiently with high quality.

One aspect of the present invention relates to a method for removing select portions of a chromosome comprising calibrating a microdissection workstation by determining the position of a micro-tool using at least two CCD cameras and recording a zero position for the micro-tool. The micro-tool is then moved to a desired microscope objective (e.g., the crosshairs of the microscope) and the position of the micro-tool in such location is recorded. The micro-manipulator then releases the first micro-tool and selects a second micro-tool. Using the CCD cameras, the tip of the second micro-tool is determined and the differences in coordinate space between the zero position of the first micro-tool and the similar position of the second micro-tool are recorded. The second micro-tool is then moved beneath the microscope objective and is properly centered by adjusting the location of the second micro-tool using the differences between the zero position of the first micro-tool. A microscope slide having a chromosome in contact therewith is positioned beneath the microscope objective at a desired centered location (e.g., at the intersection of the microscope crosshairs). The second micro-tool is then brought into contact with the chromosome at the crosshair location in such a manner that a particular chromosome locus is removed from the chromosome. The removed chromosome portions are then deposited in a receptacle. The above-described method can be repeatedly performed using additional micro-tools to accumulate a desired amount of chromosome material.

As one will appreciate, the above-method is automated such that an operator need only expend the time and effort required to properly calibrate the system using a first micro-tool and thereafter rely upon the calibrated differences between such first measurements and measurements of subsequent micro-tools in order to achieve the desired repeated microdissection process.

The present invention also includes the automated microdissection apparatus utilized in the above-described method. In one embodiment, the workstation of the present invention uses an inverted microscope with a stage micrometer mounted onto a concentric substage, i.e., wherein the axis of rotation is about the optical axis of the microscope. Such substage capable of rotating a microscopic slide within the microscope's field of view regardless of where the field of view is located on the microscopic slide. The rotating substage thus provides the ability to rotate a chromosome so as to be in alignment with a micromanipulator's micro-tool. Motorization of the various axis of the microscopic stage allows automation of the stage to facilitate microdissection of particular chromosomes, regardless of the orientation of such chromosomes.

Yet another aspect of the present invention is directed to a micromanipulation device which comprises a microscope having a stage for placing a biological sample, a rotator for rotating the stage about the optical axes of the microscope, a first rectilinear device for moving the biological sample along a first axis on the stage, such rectilinear device being accurate in its movement to within a micron, and more preferably to within about 1/10th of a micron. A second rectilinear device is provided for moving the biological sample along a second axis on the stage, similarly being accurate in its movement to within a micron, and preferably, 1/10th of a micron. An end effector is provided capable of grasping a micro-tool. A user input device inputs data to achieve one or more of the following functions: activating rotation of the stage, activating the first rectilinear device for moving the biological sample along a first axis and activating the second rectilinear device for moving the biological sample along a second axis.

Using the present micromanipulation device, a biological sample is positioned in a desired orientation for manipulation, such manipulation achieved by contact of the biological material with the micro-tool. The micromanipulation device of the present invention may further include at least one spectral imaging component in addition to the microscope, such component providing information relating to the location of a micro-tool being used in the micromanipulation procedure. For example, when two imaging devices are positioned relative to the micro-tool, information is provided that locates the micro-tool in three-dimensional space. Other aspects of the present invention include a decontamination system for reducing the contamination of a biological sample, for example, one or more ultraviolet lamps. A further aspect relates to the use of a robotic controller for translating the input data into commands for activating one or more of the rotator and/or first or second rectilinear devices. The micro-tool can be directed through the use of a joystick, a mouse, hand wheels or a computer keyboard.

Other embodiments and aspects of the present invention will be obvious to one of skill in the art with the guidance provided by the attached figures and detailed description of preferred embodiments.

DETAILED DESCRIPTION OF THE INVENTION

Robotic assisted microdissection can significantly reduce the time and skill needed for cellular and sub-cellular dissection. For example a process that takes half an hour to execute can be done in less than 10 seconds using robotic assistance. This process includes securing the micro-tool 22, verifying its tip position and configuration and executing a pre-determined cut pattern of a location identified by the equipment operator.

For ease of description, the following terms are set forth to clarify the inventor's meaning as used in this application. Microdissection as applied to the biological sciences, refers to cellular dissection and manipulation on the order of magnitude from a few cells (e.g., thirty cells or less) down to cellular organelles such as chromosomes or any segments thereof. A micromanipulator 20 of the present invention is a device that scales the operator's motion by a factor from about 5:1, more preferably 10:1, and even more preferably, 100:1. The micromanipulator 20 of the present invention allows an individual to perform extremely small, stable movements such as moving a glass micro-tool 22 up, down, in and out, left and right along the X, Y, Z, and θ axes The range of motion of the micromanipulator 20 is preferably a few millimeters in any direction and is accurate to within a few microns, more preferably to within less than a tenth of a micron and most preferably to within one hundredth of a micron. Automated microdissection refers to microdissection performed largely without human intervention. An end effector 24, in one embodiment, is a form of a gripping device designed to grasp and firmly hold a micro-tool 22. An end effector 24 may contain optional devices such as sensors to confirm the possession and/or release of a micro-tool 22. Other optional devices used in conjunction with an end effector 24 include a strain gauge, illuminator (lamp or fiber optic) to project light through or at the tip of a micro-tool 22.

As used herein, micro-tools 22 are any device manipulated by the micromanipulator 20 of the present invention and generally include glass rods or glass capillary tubes heated and drawn to a microscopic point. Glass is most often the material of choice due to the characteristics of the material being chemically inert, ductile, sterilizable, etc. The proper type of glass can be drawn to submicron points as will be appreciated by those in the art. The glass instruments, microneedles and micropipets (collectively referred to herein as "micro-tools" 22), required for microdissection and micro cloning are currently constructed manually in the lab. The skillful use of a microforge (like a de Fonbrune microforge) is used to make such instruments by forging glass rods to make microneedles with very fine tips for accurate dissection. Capillary micropipets are used with desirable nanoliter volumes for delivering micro-quantities of reagents under the microscope. A micro cloning experiment typically can require 20–30 such micropipets 22 to execute various steps of micro cloning. This is because each reaction, like enzyme digestion, phenol extraction, and ligation, will use a different micropipet 22 to avoid contamination, and the micropipet 22 is discarded after each use.

The automated microdissection workstation 20 of the present invention performs microdissection by means of micro-robotically handled micro-tools 22. In one embodiment, the micro-robot of the present invention comprises a multi-axis Cartesian and/or polar coordinate positioning system and includes a micro-robot, machine vision device 26, end effector 24 for holding micro-tools 22, single or multiple storage devices 32 for microdissected fragments and a precision microscope 28 with an articulated microscope stage 30. Preferably, the automated microdissection workstation 20 of the present invention is a self-contained system capable of performing microdissection reliably with a minimum of operator interaction. For example, an operator's interaction is ideally limited to loading of the appropriate set of micro-tool magazines 40, placing the microscope slide 42 onto the stage 30 and targeting the areas to be microdissected. As used herein, machine vision is a method of using a solid state video camera 26, such as a charge coupled device (CCD) in conjunction with a computer and appropriate algorithms that when used together, "see" an object focused onto the CCD element array. Because the CCD array is made up of a fine grid of individual sensors or array thereof, an image projected onto a CCD element is akin to a picture projected onto a measured grid whereby each picture element represents a discrete coordinate in two-dimensional space. Machine vision algorithms are software routines that can discern various elements of the projected image such as edge boundaries, converging edges to a point, centroids, etc. Software vision algorithms useful in the present invention are capable of determining characteristics of the micro-tool used, such as the point size, shape and location in three-dimensional space within the coordinate area of the CCD arrays.

Compared to manually operated micromanipulators presently available, the automated microdissection and micromanipulation device 20 and system of the present invention utilizes miniaturization of robotic systems for cellular level operations, thus allowing a technician to mount a prepared microscope slide 42, line up a region of interest with an optical target and press a button to initiate a sequence of events that results in a successful micromanipulative operation at the selected region. Applications for the present invention in the biological sciences are widespread and include, but are not limited to, in vitro fertilization, agricultural genetics, pharmaceutical development, and cancer diagnostics. The present technology is particularly suitable for cytogenetic technology and live cell manipulation, such as microinjection processes. In cancer diagnostics, the ability to isolate particular tumor cells from normal cells using the present invention provides a superior method for determining proper treatment of particular cancers. In a particular embodiment, T-cells can be isolated for use in immunotherapy to combat various disease states. Gene probes and gene chips can also be manufactured and manipulated using the present technology. Aspects of the present invention include: (i) preparation of human chromosome slides for microdissection, (ii) use of a modified fixation procedure to minimize acid damage to the chromosomal DNA, (iii) trypsin-Giemsa banding for chromosome and band identification, (iv) construction of microdissection glass needles 22 with tips in suitable sizes and dimensions, (v) proper use of the micromanipulator 20 for precise microdissection of chromosome bands, (vi) transfer and dislodge of dissected fragments into nanoliter microdrop for micro cloning, (vii) construction of capillary micropipets in various sizes and shapes to deliver and withdraw reagents in nanoliter volumes, (viii) strict control to minimize DNA contamination during microdissection and micro cloning, (ix) exhaustive phenol extraction to yield pure DNA for MboI digestion and ligation in microdrop, (x) preparation of ultra-pure and buffer-saturated phenol for extraction, (xi) achieving maximum ligation between dissected sequences and the MboI linker-adaptor molecules, (xii) execution of PCR for maximum amplification of the dissected sequences ligated to the linker-adaptor, and (xiii) purification of the short inserts and PCR products (mean length 200 bp) for the highest yield and maximum transformation efficiency.

The phenol extraction step, as an example, requires three phenol extractions performed in a tiny microdrop with nanoliter volumes, operated through a micromanipulator and visualized under a high power (100×10) microscope. Extreme care must also be taken in this step because the microdrop may be accidentally drawn into the micropipet shaft and not retrievable. Once the microdrop is lost, the whole microdissection and micro cloning process will have to start over again. It is crucial to remove the last trace of phenol from the microdrop, particularly for the final phenol extraction, to achieve maximum MboI digestion and ligation. For this purpose, a micropipet 22 is constructed with a very fine tip, sharpened at an angle so that the tip opening can rest flat on the coverslip to reach and withdraw the last trace of phenol surrounding the microdrop. After phenol extraction, the microdrop is pushed gently to another location and stored overnight with the drop facing down so that any residual phenol can be dissipated into the surrounding oil. This procedure ensures maximum removal of phenol to achieve highest efficiency in MboI cleavage and the linker-adaptor ligation reaction.

In one embodiment, the method of the present invention can be described as follows:

1. An operator selects a gene locus 36 suitable for microdissection and places a reticle target 34 on the selected area of interest;
2. The automated system 20 of the present invention picks up a micro-tool 22;
3. The micro-tool 22 is moved into the vision stage 38 consisting of at least two CCD cameras 26 operatively associated with a computer vision software module. The process locates the micro-tool's tip in three-dimensional space and provides its positional relationship to the target reticle;
4. The micro-tool 22 is moved to a predetermined coordinate of the reticle target 34 and a pre-programmed stroke of the micro-tool 22 is thus performed to achieve microdissection of the gene locus.

The workstation platform 20 and enclosure of the present invention is designed to have dimensional stability, resistance to vibration internal to the platform and to isolate the system from external vibration. The enclosure part of the platform provides a contamination free environment and thermal stability. Within the platform are heating and cooling elements as well as environmental conditioning devices such as strategically placed UV lamps for eliminating DNA contamination. External to the system is a HEPA filtration system, etc. To achieve desired thermal stability of the platform the temperature is stabilized within +/−2 degrees Celsius. The platform is preferably constructed of a heavy material, such as granite or a composite material, with low thermal expansion characteristics. This provides dimensional stability and resistance to internally generated sources of vibration. Mounted on the heavy/massive base are the elements of the system, including but not limited to the microscope 28, robot 25, vision units 26 and vial holders 32.

The enclosure is insulated and ergonomically compatible for use by the operator.

The Cartesian coordinate robot 25 of the present invention is very precise, manufactured from very stable materials, low friction linear bearings and linear, rotary or piezo electric motors capable of sub micron positioning resolution. The platform is designed to resolve to ⅛ micron or better and the position repeatability is as important as the position accuracy. There are four primary axes X,Y,Z and Theta. In a preferred embodiment, the Theta axis is "soft" and when pushed on it will give, only to return to position when the force is released. This helps in establishing a spring tension on the micro-tool 22 mechanism when it contacts the microscope slide cover. The robot axes 25 are long travel compared to any current micro-manipulator. The purpose for this is to perform all of the related tasks germane to automated micro-dissection. The travel distance on the X and Y axes are between about 5 and 12 inches, preferably approximately 7 inches each. The Z axis travel is between about 3 and 7 inches, preferably around 4 inches. The Theta axis moves the end effector 24 and micro-tool 22 from horizontal to vertical between about 1 to 180° and preferably better than 90° of travel.

The micro-tool 22 is grasped in a reliable, repeated fashion by the end effector 24. Fiber optic or lamp illumination of the end micro-tool 22 end may be used to illuminate the micro-tool 22 tip. This can be helpful in locating of the tip manually, as well as during computer vision identification. Infra-red tracking can also be used to follow the micro-tool tip. The end effector 24 may, in addition, have a high voltage contact designed to charge the micro-tool 22, thus imparting desired static electric charges on the tool 22 and/or subject to achieve desired pick-up and/or manipulation.

One of the current difficulties in manual microdissection is the lack of static attraction necessary to lift the sample from the slide to the micro-tool 22. One reason for this is the amount of light focused in the area which has a tendency to neutralize the charge on dielectric materials such as glass. By charging the micro-tool 22 and the microscope slide 42 oppositely, the material can be statically held when a micro-dissection is performed. Currently, manually performed microdissections have to be monitored for reliability. The micro-tool 22 has a tendency to push the chromosome material without the material sticking to the micro-tool 22. The operator must then place the micro-tool 22 over the sample and press the tool 22 down onto the sample to "stick" the sample to the tool 22. By selectively applying high voltage (600 to 24,000 volts) to the glass micro-tool 22 and oppositely to the slide 42, the material easily and reliably adheres to the micro-tool 22. By turning the power off or even reversing the polarity, the sample can be removed non-tacitly. Thus, this eliminates the need to replace the micro-tool 22 after each identical sample gathered.

The workstation 20 of the present invention uses an inverted microscope 28 with a stage micrometer 30 mounted onto a concentric sub-stage that rotates about an axis of rotation that is identical to the axis of the microscope's optical path. This can rotate the microscope slide 42 under the microscope's field of view maintaining precise spatial reference to the optical cross hairs on target. The advantage to this feature is that a chromosome 36 (or other subject to be manipulated) can be aligned such that the arms of the chromosome 36 are perpendicular to the micro-manipulator's angle of attack. The sub-stage's rotary axis and the stage micrometer 30 may be motorized in some embodiments. Indeed, if it is desirable to rotate the stage 30 and further use the stage micrometer, motorizing the three axes allows computer translation of the operator's turning of the stage micrometer 30 dials into apparent matching vectors even though the stage micrometer 30 is turned at an angle.

Figure 1:
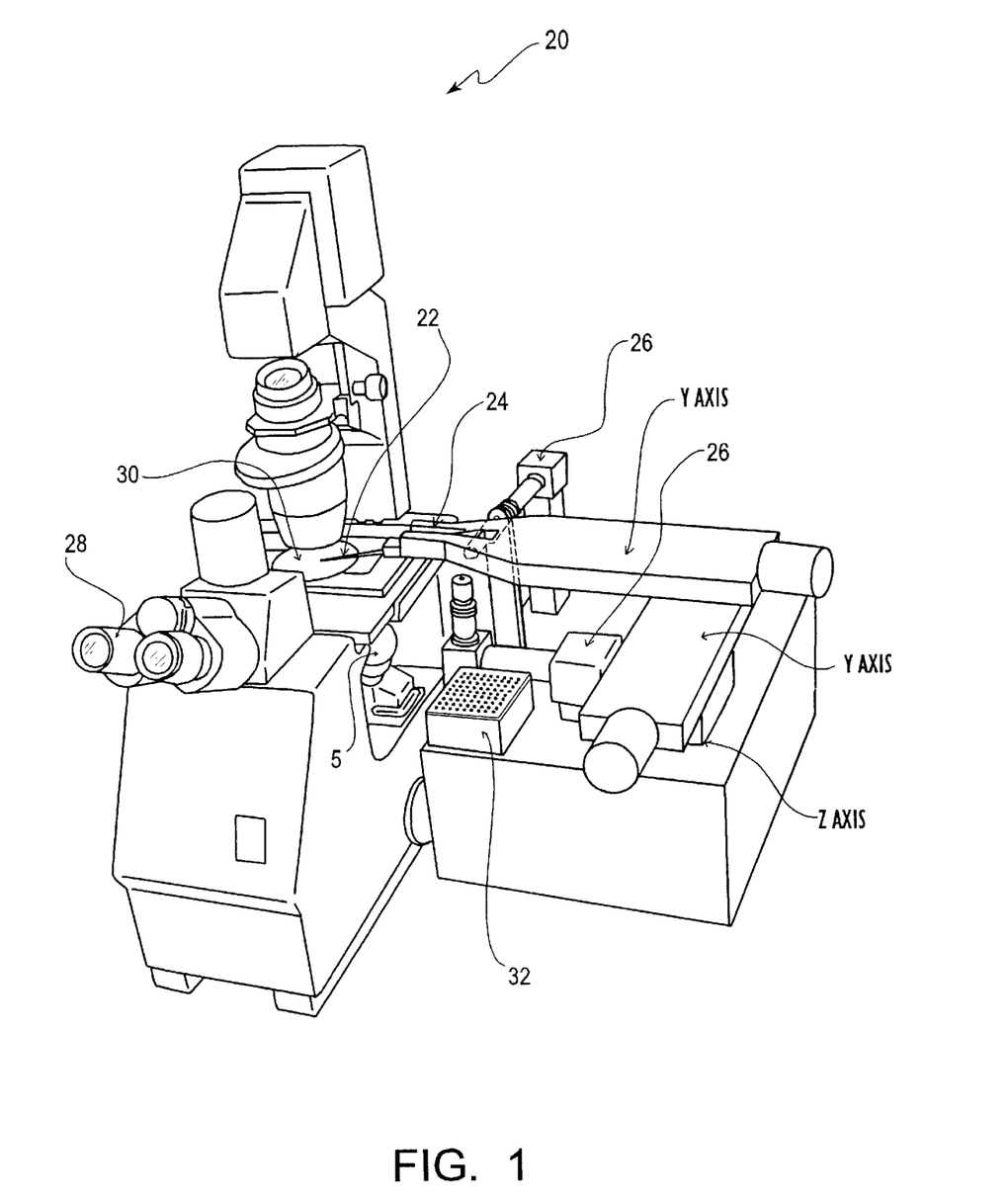
FIG. 1 is a perspective view of one embodiment of the micromanipulation device of the present invention.
Figure 2A:
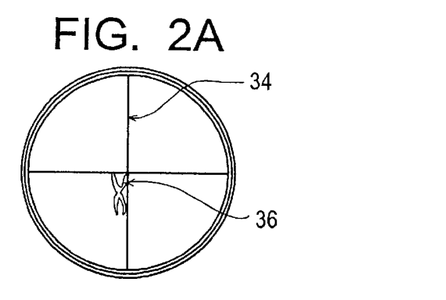
FIG. 2A illustrates a view through a microscope showing a chromosome portion centered over an eye piece reticle.
Figure 2B:
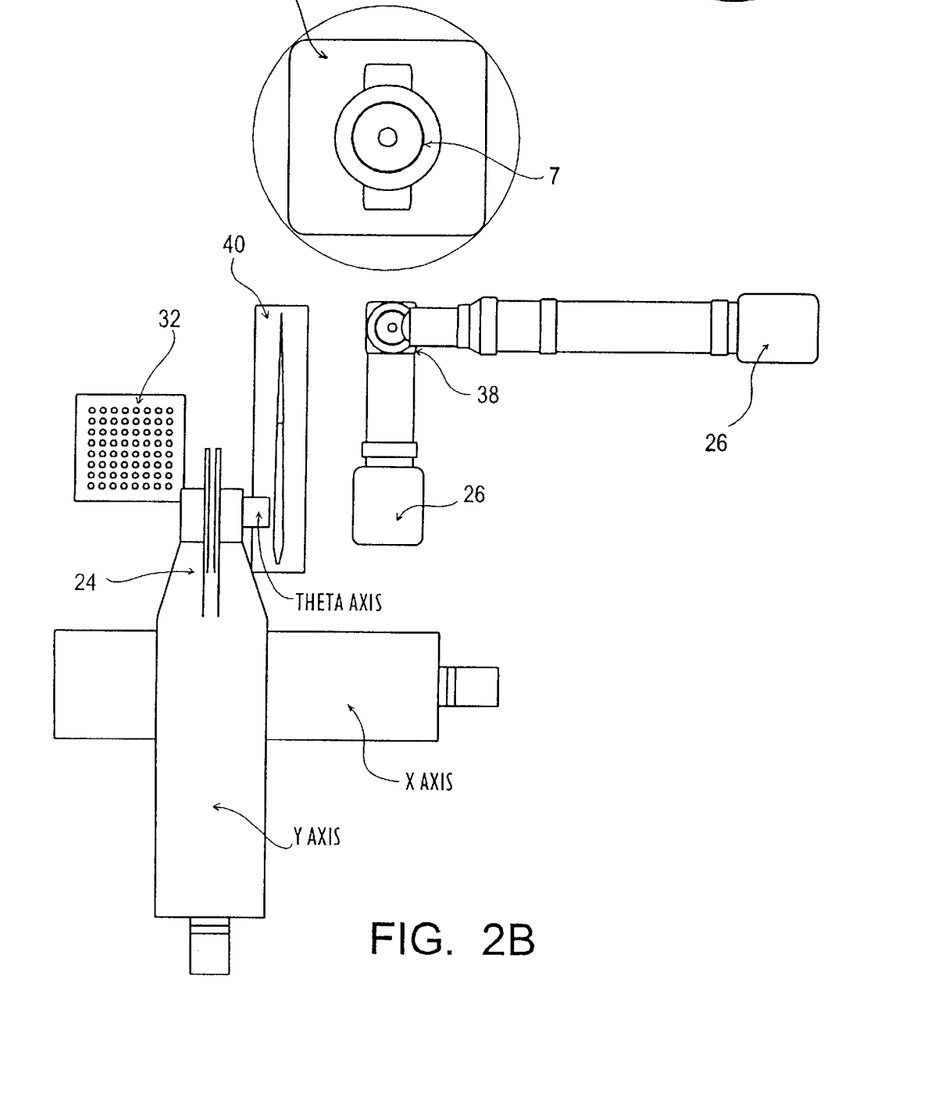
FIG. 2B is a top view of one embodiment of the present apparatus showing positional relationship between various components of the present apparatus.

In order for the microscope's optical system to perform such operations as microdissection and perform such operations repeatable to the degree of precision necessary, the objective turret 5 (FIG. 1) must have a precision detent that registers each of the objectives 7 (one of which is shown in FIG. 2B) of the present invention each time a different one of the objectives is chosen. The best method for accomplishing this is to have the turret 5 mechanically designed to be precise and repeatable on its axis and to have a precision spring loaded ball detent (not shown) whereby the final resting position of the turret is confirmed by means of an optical encoder (not shown). That is, an optical encoder with index marks corresponding to the turret positions may be used for confirming an objective's position. In an another embodiment of the present invention, a motorized turret 5 can be substituted for a turret with a detent. Although sharing the same encoder features and precision features, the added advantage of a "hands off" operation may provide greater reliability. That is, the operator would not be touching, bumping or otherwise interfering with the precision mechanism and thus misuse may be reduced.

Using the present invention, an automated microdissection can be performed in a few seconds. Because of the proposed methods of microdissection often require a new micro-tool 22 for each operation, manually attaching each micro-tool 22 to the robot 25 becomes an impractical bottleneck. Thus, a preferred embodiment utilizes a magazine 40 holding several standardized micro-tools 22 to save time, eliminate handling of the micro-tool 22 and to facilitate quick micro-tool 22 changes. The magazine 40 preferably has a high holding capacity, preferably holding loo micro-tools 22 or more. Micro-tools 22 can be made, graded by tip size and loaded into the magazines 40. The advantages are safe, non-human handling of the micro-tools 22, and the speed and storage of like size and shape micro-tools 22. All of these advantages improve dissection cycle times, reduce the possibility of contamination and insure similar size microdissections.

To determine the micro-tool 22 point size and position, relative to a calibration standard, a vision stage 38 is used having two CCD cameras 26 equipped with microscope lenses. Since the micro-tool 22 is best angled in the vertical axis, the system looking up (or down) at the micro-tool 22 is pre-angled to be perpendicular to the plane of the micro-tool 22. Using black or colored glass micro-tools 22 mitigates difficulties in lighting of the vision stage. Using a flat field laser and detector, the micro-tool 22 is located in 3D space without undue concern of lighting or focus. The vision stage's 38 automatic tool calibration alleviates prior difficulties relating to the inconsistency of a micro-tool's 22 tip location. One CCD camera 26 looking at the micro-tool 22 point from the side places the point in the Z axis plane. The other CCD camera 26 looking up places the micro-tool X and Y axes planes. The computer vision task involved is well within computer based vision technology and will be easily available by one of skill in the art.

In order to calibrate the micro-tool 22 path with respect to the vertical or z axis relative to a standard slide or coverslip, the standard slide or coverslip can be uniformally stained for use in determining the Z position of the micro-tool during initial calibration. When a microdissection is performed, a certain amount of downward force must be exerted against the cellular material in order to dislodge or scoop sample material from the slide. In order to interactively arrive at an appropriate Z position relative to the slide or coverslip surface, the stained slide can act as both a focusing medium for the operation and provide a test media for determining the proper force during the operation. That is, calibration may be performed wherein the micro-tool tip applies sufficient pressure against the slide to scrape off the stain, but not damage the micro-tool tip.

Once such a calibration of the Z axis is performed, the resulting calibration values may be used with determining an appropriate micro-tool path for other slides. That is, when a new slide is placed onto the microscope stage, a commercial laser depth sensor can be used to determine any significant deviation in the Z axis within the field of view of an objective. Note that the Z axis deviation from one slide to the next is unknown. This laser depth sensor will provide information that will be read by software of the present invention, and factored into the coordinate stack used in moving the micro-tool (via the effector), as one skilled in the art will understand.

Several designs of vial holders 32 can be used in the present method. A circular row of vials can be advanced one at a time to be exposed to an opening when the gene sample is being deposited. A rectangular grid of vials 3 that are linked together, as commonly used in PCR processing, can be placed in rows. Either a movable cover that exposes a particular vial or a motorized sub-stage can move the appropriate vial to a stationary opening.

In yet another aspect of the present invention, in order to facilitate rotational orientation of a sample to be microdissected, a microscope stage 30 is provided having a rotary stage concentrically rotating about the axis of the microscope's optical path. Movement along the X, Y, Z and theta axis are then made possible, as described above, with the addition of the ability to rotate a sample into desired position with a micro-tool 22 orientation. A return lock mechanism can be utilized (for example an embedded ball detent) to insure that the microscope stage 30 returns to an original position after a microdissection operation. Such return mechanism can be motorized, as can the rotary stage 30 described above.

Micro-tools 2 of the present invention are preferably made from glass which is drawn, as in pulling through a thinning process, through a liquid matrix rather than through the air, thus increasing the surface tension. Micro-tools 22 are preferably presorted for size, dimensions, etc. prior to loading them into a magazine 40 for use in a repeatable microdissection operation.

The micro-tools 22 mentioned above can be of any color, size or material, but preferably have relatively uniform color, size and calibrated tip configurations. For example, micro-tools 22 preferred in the present invention are made from opaque glass or similar material with colors added to add contrast for easier vision usage. Using side lighting, for example, use of fiber optics can be useful in illuminating the tip of any micro-tool 22 used. Moreover, the electrical charging and/or warming of the micro-tool 22 can be achieved for infrared and/or electric field proximity location operations. Although the use of CCD cameras 26 for sizing and locating micro-tool 22 tips is described, it will be clear to one of skill in the art that other devices can be utilized, such as lasers, vision systems and other position orienting devices.

In embodiments where it would be desirable to have the micro-tool 22 attract and/or repel material to be dissected, static attraction of microscopic material can be utilized. Such a process to impart such static attraction is similar to xerographic attraction. For example, the voltage supplied to a micro-tool 22 could be between 1 to 24,000 volts, with 6,000–12,000 being more preferred. A static drop off of the material being microdissected can be achieved by grounding or reversing the charge on the micro-tool 22. Using this static attraction/repelling method, an operator is able to replace the steps of scraping and/or lifting of microscopic material (such as chromosomes, small electronic components, etc.) to achieve accumulation of desired material. In other embodiments, the microscope slide 42 itself is made of a non-stick material or is coated to achieve desired characteristics to facilitate the attraction/repelling of static charge. Using the present method, an operator is able to create a dry pile of micro-dissected objects, such as chromosome sections. For example, by placing a charged metal needle directly under a drop off area, such as a receptacle, glass cover slip or miniature sample tube, the oppositely charged particles on the micro-needle 22 are removed (e.g., jump off) to the closest location above/below the charged needle.

Computer based scraping algorithms can be utilized in conjunction with a touch screen pin to define an area within a microscope's 28 field of view. The algorithm is able to trace the outline described by the touch screen pattern and direct the methodical positioning of a micro-tool 22 to a particular area so that the micro-tool 22 can "scoop" or otherwise make contact with the subject material.

Microdissection Process Description

1. Preparation

The operator places several pre-formed micro-tools 22 into a holding magazine 40. The operator then places the slide 42 containing the sample material 36 on the stage of an inverted optical microscope 28.

2. Location of the target sample once the slide 42 is in place, the operator searches for a suitable sample for dissection 36. The sample 36 then is centered over an eyepiece reticle 34 much like a rifle scope is pointed at a target. The reticle target 34 can be shaped like a rifle scope target, or it may represent a cut area using a rectangle.

3. Micro-tool calibration

Figure 3:
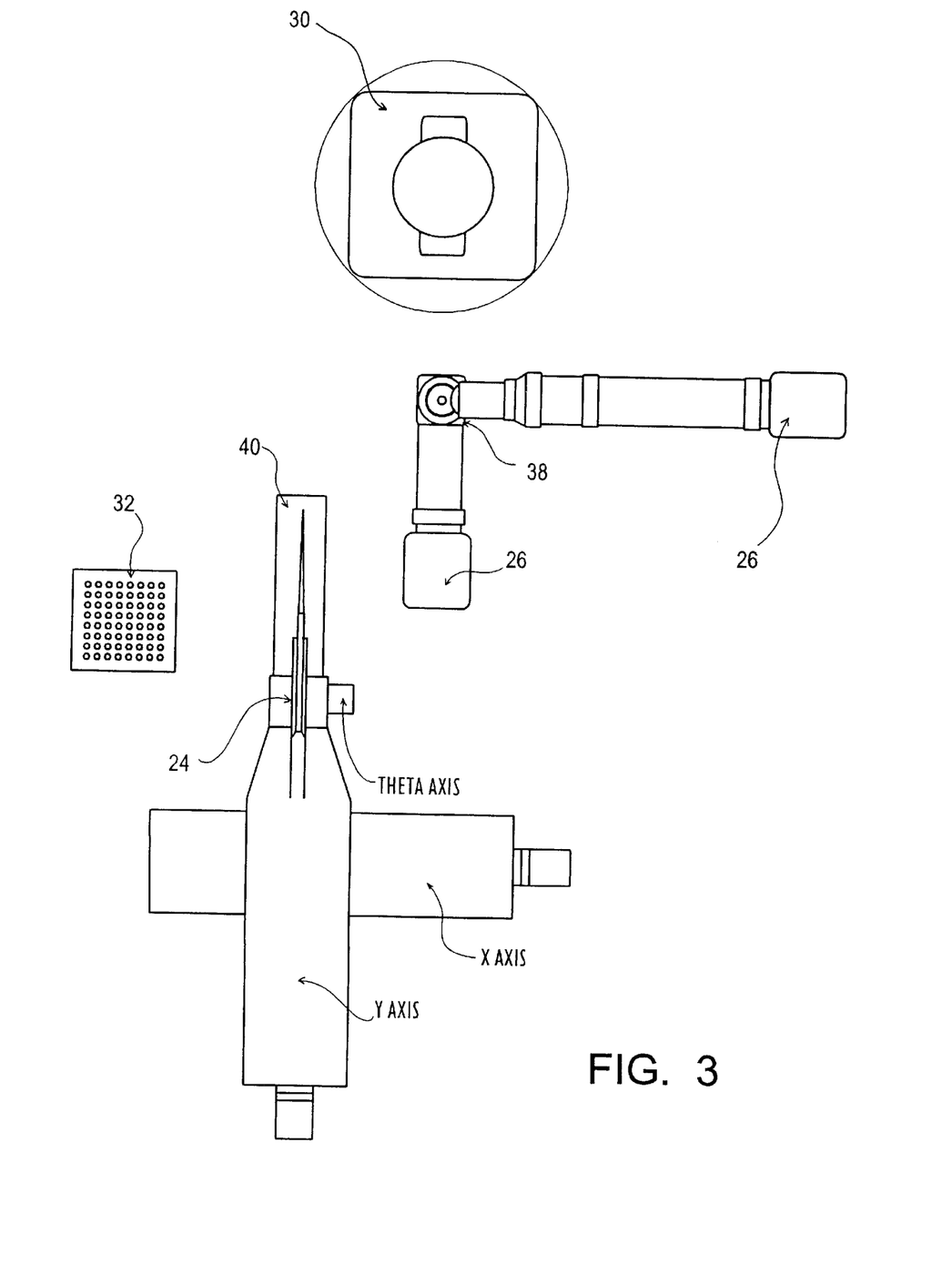
FIG. 3 illustrates how a micro-tool is grasped in a micro-tool clamp using the present apparatus.
Figure 4A:
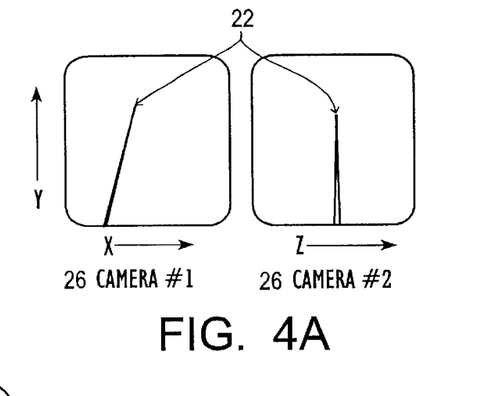
FIG. 4A illustrates the respective views of two CCD cameras mounted at 90° from each other, providing positions within which to locate a tool point in three-dimensional space.
Figure 4B:
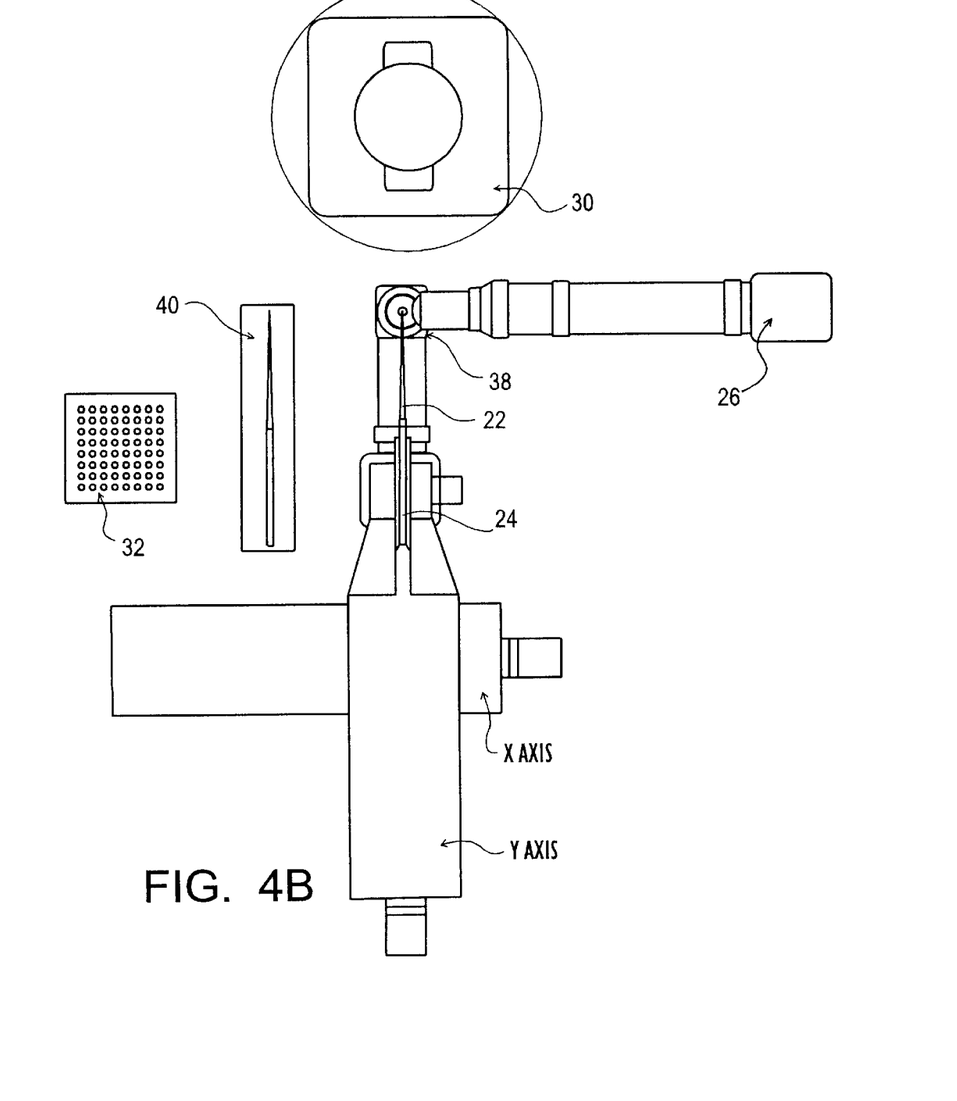
FIG. 4B is a top view of the present apparatus wherein the micro-tool grasped by the micro-tool clamp is positioned with its point on the vision stage.
Figures 5A, 5B:
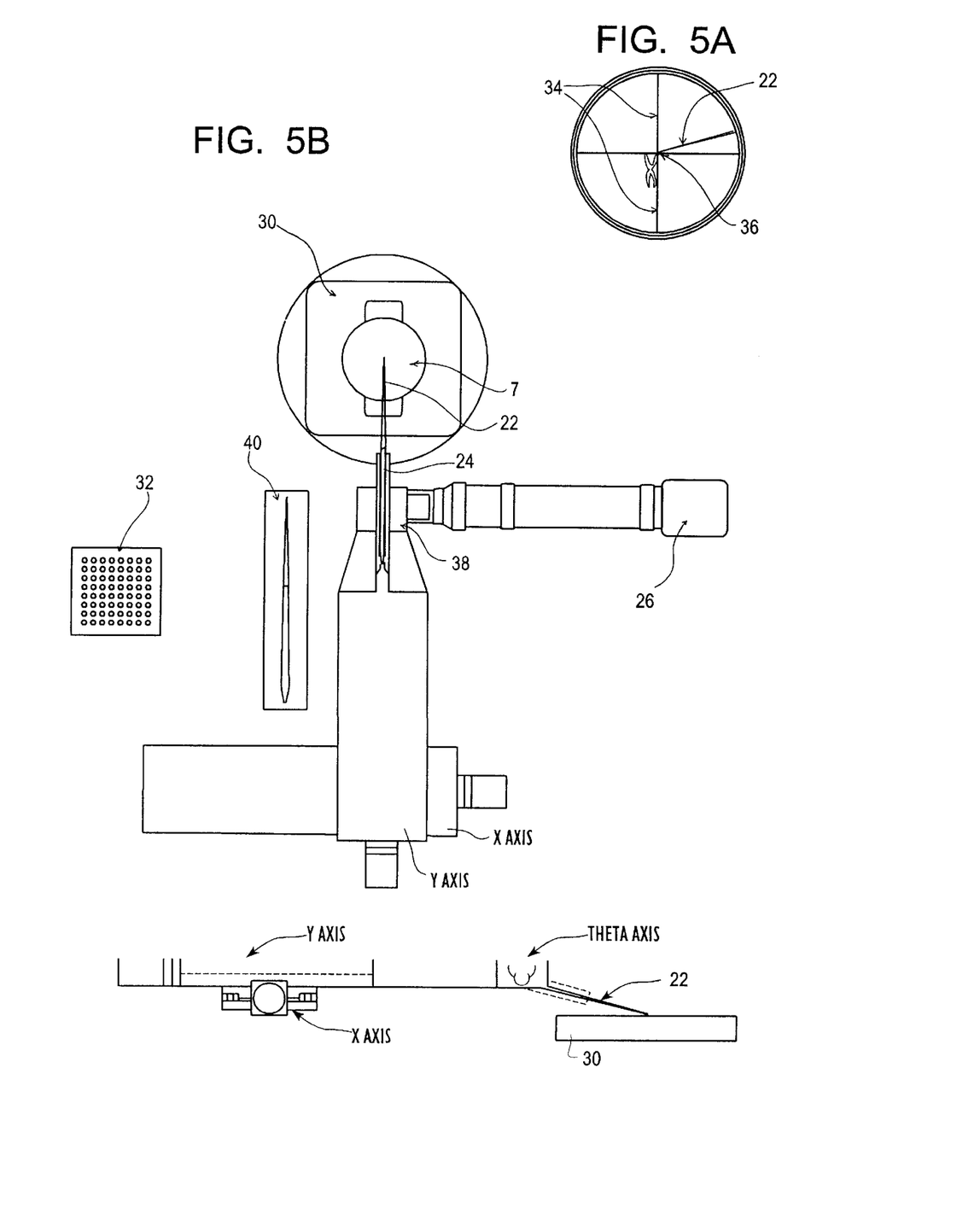
FIG. 5A is a view through a microscope of a chromosome with a micro-tool point at a desired chromosome loci.
FIG. 5B is a top view of the present apparatus with the micro-tool contacting the microscope stage to remove desired portions of a chromosome.

The micro-tool 22 is picked up by the robot 25 and the tip is positioned in a calibration area 38. The calibration area can consist of two CCD cameras 26 mounted at 90 degrees from each other with lenses and lighting suitable for seeing the micro-tool point. Once in the calibration area 38, a vision software program locates the tool 22 point in three dimensional space (X, Y and Z) and notes the tip geometry.

4. Microdissection

Through a prior calibration process, the motion control software has located the coordinate location of the reticle 34, microscope stage 30 and the coordinate space of the tool calibration area 38. With this information, the micro-tool 22 is moved from the calibration area 38 onto the microscope staging area 30.

Micro-Robot Description

Gene locus dissection is one of the uses of the micro-robotic aspects of the present invention. The X, Y and Z stages for the micro-robot 25 have at least 0.5 micron resolution and up to about 0.1 micron resolution. In order to achieve this precision and have the ability to move rapidly from stage to stage, a very fine pitch servo driven ball screw is used along with a high count rotary encoder for each axis. A 1 mm pitch ball screw with an 8000 quadrature count encoder yields a step size of 0.000125 mm or 0.125 microns. In order to ensure smooth, repeatable motion, a precision cross roller way bearing unit is used to guide each axis. Motor speeds of 3000 rpm yield a linear motion of 50 mm per second at maximum velocity. This ensures speedy handling when necessary.

A theta axis is used to angle the tip properly for microdissection as well as depositing specimens into appropriate vials 32. Rotary axis motion is more coarse than linear motion in most cases. A practical resolution would be ¹⁄₄₀₀₀ of a circle. This yields about 25 micron steps at the tool 22 tip. Fine Z axis motion comes from the robot's 25 Z axis.

In one embodiment, the micro-robot's 25 vision stage 38 consists of two high resolution CCD cameras 26 mounted at 90 degrees from each other. A microscope objective and secondary lens set near the camera 26 gives the camera's resolution similar to that of the Y, Y and Z stages. Using high contrast back lighting, the vision software is able to locate the micro-tool 22 in X, Y and Z planes.

The microscope stage 38 preferably has a rotary axis in addition to the normal X and Y axes. In this case, the X and Y stages are interior to the rotary stage such that when the stage is rotated, the object in the microscope's view remains in the same X and Y space. This eliminates one major problem with conventional micro-manipulators. Conventional micro-manipulators need to be moved manually around the microscope in order to arrange the correct angle of attack for a given dissection.

While the above description of the present invention has been largely directed to biological sciences, other aspects of the present invention relate to the use of the micromanipulator device and method in other fields, such as electronics, microrobotics and indeed, in any field where manipulation of small and/or microscopic particles is required.

Note that the present invention may be particularly useful in combination with a technique developed by Aaron Bensimon et al. at the Pasteur Institute in Paris, France, wherein this technique straightens the typical curliness of DNA molecules.

The principle behind Dr. Bensimon's technique for molecular combing is disarmingly simple. First, DNA molecules are dissolved in water. Then a chemically treated glass slide is dipped into the liquid and slowly drawn out. The pretreatment causes the ends of the DNA molecules to stick to the glass. As a result, the receding surface of the water pulls the DNA into straight filaments on the glass plate, much as long hair is pulled down a swimmer's back as the swimmer emerges from a pool. The DNA is combed straight by the surface tension of the water, a force just powerful enough to overcome the molecule's natural springiness without ripping its anchored end from the glass.

EXAMPLES

The following are experimental methods used in the present invention:

Human cells used for microdissection

The human lymphoblastoid cell line GM03714 (46, XX; Cell repository, Camden, N.J.) which grows well and displays consistent, normal karyotype was used to construct microdissection libraries. The microdissection libraries described herein were constructed from this cell line.

Chromosome slide preparation

Mitotic cells from GM03714 were harvested and fixed twice, 510 min each, in 100% methanol instead of acetic acid to avoid possible DNA damage. For better chromosome spreading, the fixed cells were dropped onto the slide and while they are still wet, a dilute acetic acid mixture (e.g., methanol:acetic acid 9:1) was rinsed through the cells before complete air-drying with the aid of a fan. This procedure increases chromosome spreading and yields cytoplasm-free metaphases. The chromosomes were trypsin-Giemsa banded for accurate identification and dissection.

Evaluation of a microdissection library

The quality of a microdissection library was evaluated at two stages during micro cloning.

(i) Evaluation of the PCR products immediately after amplification of the microdissected sequences.

In each micro cloning experiment, a control drop without dissected fragments was carried along identically with the sample drop. After PCR, small samples of the PCR products from both drops were tested by mini-gel blot hybridization using labeled total human DNA. The control drop did not exhibit any hybridizing signals whereas the sample drop showed significant hybridization. (If the control drop displays a light smear of hybridization, the experiment should stop and a new round of microdissection and micro cloning should be initiated.)

(ii) Evaluation of the library after transformation.
  (a) The proportion of repetitive sequence micro clones is generally 40–60%. If the proportion is significantly lower than this level, the presence of contaminant (non-human) DNA is indicated.
  (b) The number of micro clones containing no insert is generally low, less than 5%. If the number is high, another transformation experiment may be conducted.
  (c) Southern blot hybridization of single-copy micro clones to DNAs containing human, single human chromosome hybrid, and the rodent parent, as described above. If a microclone shows positive hybridization to human and the hybrid, the microclone is usually derived from the dissected region. The test in (c) is most crucial for demonstrating a satisfactory library. A good microdissection library should contain 50% or more single-copy micro clones derived from the dissected region. If the yield is significantly lower than 50%, the isolation of large numbers of single-copy micro clones from the library will become more tedious and time-consuming. However, this library may still be useful as FISH painting probes for cytogenetic analysis.

Human chromosome region-specific libraries can be constructed by microdissection of specific chromosome regions followed by the MboI linker-adaptor micro cloning technique. Chromosome fragments are microdissected, treated with proteinase K, extracted with phenol, cleaved with MboI, and ligated to an MboI linker-adaptor. All these steps and reactions are conducted on glass slides in nanoliter microdrops aided by micromanipulator and microscope. The ligated sequences are PCR amplified and cloned into pUC19. Large libraries with hundreds of thousands of independent micro clones can be obtained.

Using the present invention, the gene-richest regions in the human genome can be selected for dissection. The resulting libraries can be evaluated to ensure high quality and further developed for various applications, including Pi isolation, contig assembly, region-specific STSs preparation, high resolution mapping, microsatellites isolation, subchromosomal CDNA isolation, positional cloning, and chromosome regional painting.

In preparation for use of the microdissection workstation 20 to collect chromosome segments, prepared slides 42 with target genetic material 36, a magazine 40 of sterile, size-matched micro-tools 22 and a vial holder are brought to the work area.

Initially, several coordinate locations are programmed into a table for the software to reference during the automatic operations subsequently performed. The operator moves the robot 25 axes interactively using a joystick or similar device to these locations. Once the robot 25 is at the desired position, the operator records the coordinate location (e.g., by pressing the appropriate key or button). A representative calibration sequence is as follows:

The operator moves the end effector 24 to the micro-tool magazine 40 and closes the end effector onto the end of the first micro-tool 22 in the magazine 40. The operator presses the appropriate key or button to record a first position of the micro-tool 22 tip.

With the micro-tool 22 attached to the end effector 24, the operator moves the micro-tool 22 point into the coordinate space of the vision system 38. In this step, the vision system images are displayed onto a computer screen allowing the operator to center the tool 22 in the three dimensional coordinate space of the vision system 38. The operator presses the appropriate button or key to initiate the recording of this position. In addition to this, the vision system captures images of the micro-tool 22. This establishes a relative zero location for the tool 22 point to be compared against subsequent micro-tools 22 used in the automatic mode.

The micro-tool 22 point is moved from the camera area 38 through a "safe path" that is recorded by the computer system into the coordinate space of the microscope slide 42 and optical center. When the micro-tool 22 point is set at the correct location, the operator again presses the correct button or key to record this location. The Z coordinate location is defined by the micro-tool 22 point in contact with the microscope slide 42 surface. This preferably includes some micro-tool 22 flexure to insure enough downward force to properly excise the genetic material 36. The X and Y coordinate position of the micro-tool 22 point is set in relationship to the microscope reticle 34 (e.g., cross hairs).

Figure 7:
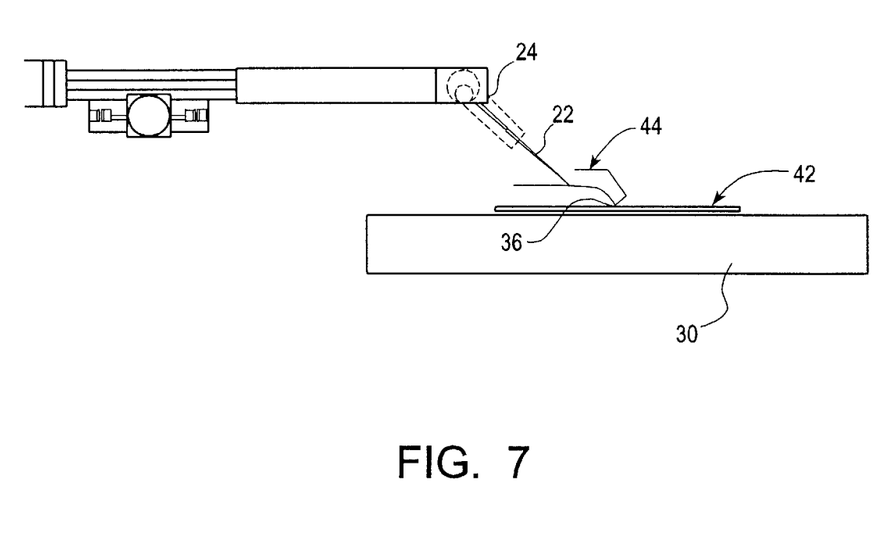
FIG. 7 is a side view of the present apparatus illustrating the desired programmed path of a micro-tool point as it comes into contact with a desired gene locus and is thereafter removed to a depositing receptacle.

Once this position is recorded, the operator can either continue to define additional points interactively or input the cut path 44 by manually inputting relative coordinates of a desired cut path 44. For example, the operator may want to make a short stroke, raise the micro-tool, advance two microns and lower down onto the slide to make contact between the genetic material 36 and the underside, rather than the point, of the micro-tool. This practice is common in manual microdissection.

Figure 6A:
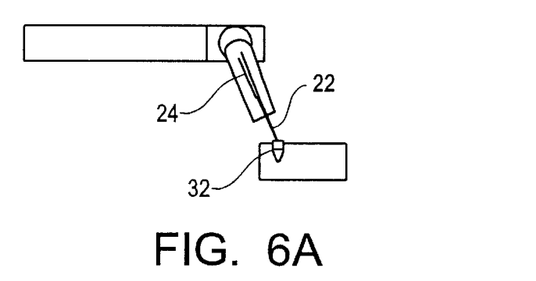
FIG. 6A is a side perspective view of how the present apparatus is positioned with the micro-tool to a receiving vial wherein the chromosome material is deposited therein.
Figure 6B:
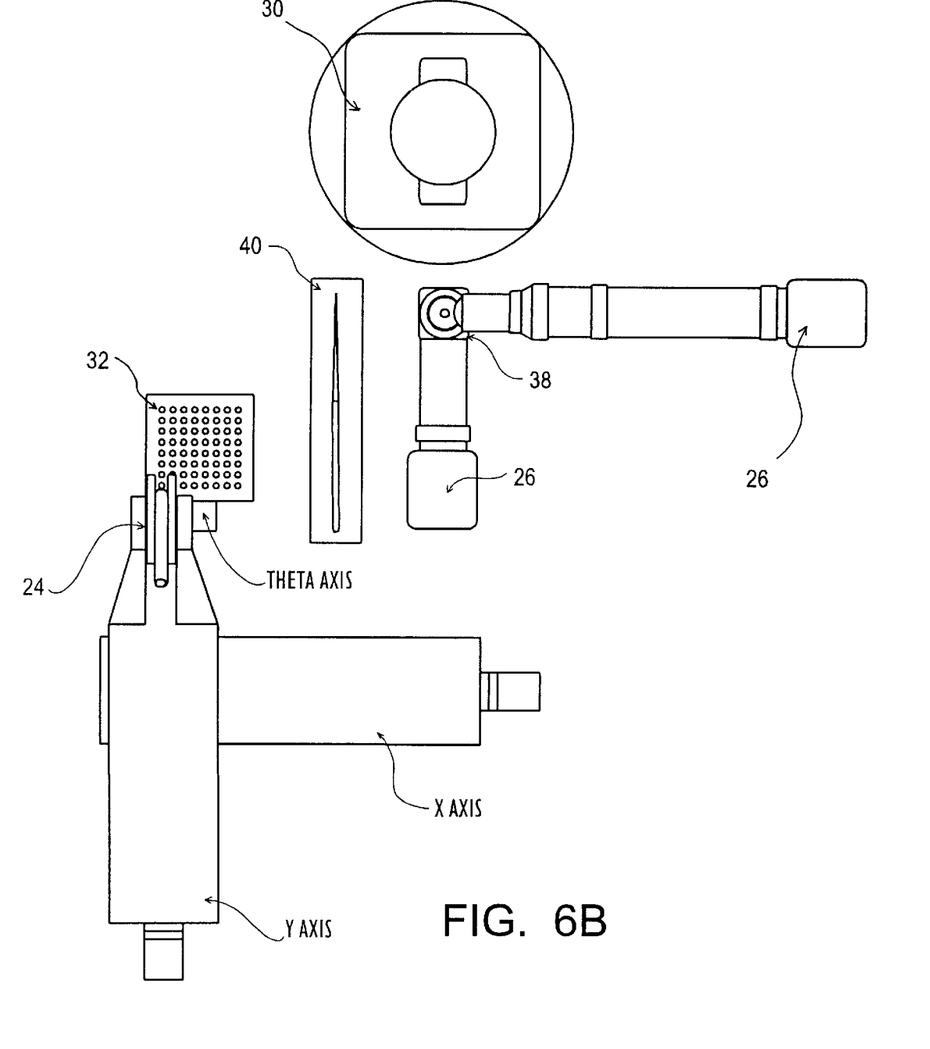
FIG. 6B is a top view of the present apparatus illustrating the deposit of chromosome material into sample storage vials.

After the genetic material 36 is secured, the operator moves the micro-tool 22 point to a desired location (e.g., the drop off coordinates). A special series of steps can be recorded to drop off the genetic material. One proposed method is to break the micro-tool 22 tip (including the genetic material) off into a vial. The glass tips can be separated out in subsequent processes.

If the tip is to be broken into a vial 32, the last location the operator moves to is a disposal area for used micro-tools 22. Again, the location is recorded by pressing the appropriate key or button.

Once the system has been calibrated, subsequent operations are very simple. For example, to perform ten microdissections of the same gene locus 36 and deposit them into the same vial 32, an operator would be the following steps:
1) Place a prepared slide 42 onto the microscope stage 30;
2) Locate the appropriate chromosome;
3) Center the reticle 34 crosshairs over the gene locus 36;
4) Rotate the concentric substage to the proper orientation;

5) Press the appropriate button or key to initiate the dissection. At this moment, the robot 25 picks up a micro-tool 22 from the magazine 40 and moves the micro-tool 22 point into the vision area 38. The position of the new micro-tool 22 point is compared to the original calibration. Any difference in position between the original calibration and the new micro-tool's coordinates is adjusted. mathematically so that the new micro-tool 22 can be positioned appropriately on the microscope slide 42. The micro-tool follows the predetermined safe path 44 to the microscope slide area 42, performs the microdissection, deposits the genetic material 36 into the vial 32 and disposes of the micro-tool 22.

6) Find a new target cell; and

7) Repeat Steps 2 through 5 until enough samples are gathered in the vial 32.

As another example, an operator desiring the sequential dissection of ten gene loci 36 from an entire chromosome using a different vial 32 for each locus, would perform the following steps:

1) Choose sequential dissection sub-routine for 10 segments;

2) Place prepared slide 42 onto the microscope stage 30;

3) Locate the appropriate chromosome;

4) Center the crosshairs over the first gene locus 36 (likely at one end);

5) Rotate the concentric sub-stage to the proper orientation;

6) Press the appropriate button or key to initiate the dissection;

7) Center the crosshairs 34 on the next gene locus 36;

8) Press the appropriate button or key to initiate the dissection;

9) Continue until the sequence is completed; and

10) Choose the next identical chromosome and re-initiate the process until the proper number of samples have been gathered for each vial 32.

In this example the microdissections are performed as in the above example except that each new sample is deposited into a new vial 32 until the 10 vials have been sequenced. By re-initiating the process on the next cell, the same vials 32 are re-sequenced to gather a significant number of samples in each vial 32.

Other aspects of the present invention include the interactive tracking of a micro-tool 22, especially when the micro-tool 22 is in the field of view of a microscope 30. A secondary zoom lens may assist in providing a beam split image to be conveyed to a vision camera 26 of the image of the moving micro-tool 22. An autofocus mode may be utilized to track the micro-tool 22 as it moves across the microscope slide 42. Indeed, it is possible to have a microscope lens above an inverted oil immersion microscope lens for this purpose. An additional CCD camera 26 and lens system can be utilized to determine a detail of the Z axis position of a micro-tool 22.

Other embodiments of the present invention utilize two microscope systems wherein an inverted microscope and an upper microscope lens system are used in conjunction with video cameras and beam splitting optics to provide light back through the optical system in order to cross compare image types. Light projected up from the bottom side is capable of backlighting or phase lighting (dark field) a micro-tool 22. Top lighting of the micro-tool 22 allows a second video camera to follow the micro-tip tool 22 while providing illumination for the biological material, thus allowing an operator to view material from both the top and bottom sides. Still other embodiments involve the use of flat beam lasers with appropriate detectors so that the Z axis position of a micro-tool 22, as well as X and Y axis positions can be located for the relative positioning of a micro-tool 22. In one embodiment, lasers using a rotating prism or mirror arrangement sweep a relatively full field, with such lasers, prisms and mirrors providing a "wobble" to move a fine laser beam up and down in order to fulfil a Z axis position requirement. Such a system provides for fine resolution of the X, Y and Z axis positions of a micro-tool 22 and the monitoring thereof. Finally, a converging scanning laser pattern can be utilized to determine distance and size. For example, a thin visible laser scanning across the field of a micro-tool 22 can be used in association with the CCD camera 26 which may rely upon the distortion in the laser line to determine the position and size of the micro-tool 22.

As will be appreciated by those of skill in the art, use of a fully integrated, menu-driven motion control software package capable of operating in real time on a PC allows coordination of motion control and data inputs and outputs through a user programmable macro control language. A range of pre-programmed procedures can be readily developed, for example, a researcher may require several dissection widths from 1 to 10 microns. Images conveyed through a CCD camera 26 can be recognized and a center or end point can be positionally determined. The software utilized is capable of switching from one CCD camera 26 to a second CCD camera 26, thus determining X, Y and X, Z positions, respectively. Again, in a preferred embodiment, the microscope stage 30 has a rotary axis in addition to the normal X and Y axes. The X and Y stages are preferably interior to the rotary stage such that when the stage is rotated, the object in the microscope's 28 view remains stationary in the same X and Y space. This eliminates a major problem with present micromanipulators which need to be moved manually around the microscope in order to arrange the correct angle of attack for a given dissection.

A typical path 44 for a micro-tool 22 in a microdissection process begins with a relatively high course above a microscope slide 42. The micro-tool 22 is programmed to plunge into the slide 42 surface in a "S" curved path to minimize the impact shock of the micro-tool 22 against the slide 42. In a programmed "cut path" 44, the microsection is sheared from the chromosome and peeled away, adhering to the micro-tool's tip by van der Waal forces.

In other embodiments of the present invention, instead of dissecting a sample (e.g., a biological sample), a micro-tool such as a micropipet may be used by the present invention for depositing a minute amount of a sample in a precise location to within plus or minus 0.1 microns of the desired location. The present invention as described for dissecting hereinabove needs to be substantially only modified by utilizing a micropipet and integrating a component for controlling the uptake and extraction of the sample from the micropipet. Accordingly, this embodiment may be used for the following (non-exhaustive) list of applications:

a) building a desired protein from amino acids, wherein each amino acid is three-dimensionally positioned in a desired location for bonding into the protein molecule to be constructed;

b) medical applications for the treatment of abnormalities, disfunctions and/or diseases, wherein a sample or dosage of a medically active substance is delivered from a micropipet to a precise tissue location (e.g., to within plus or minus 0.1 microns);

c) micro component fabrication, wherein the sample from the micropipet is delivered along predetermined paths for etching such paths into the base material (e.g., silicon) of the electronic component.

Another embodiment of the present invention may be used for the assembly of micromachines. In providing this capability, the present invention may utilize micro-tools of various types; e.g., grips, wrenches, heating elements and/or rotary devices (devices such as for drilling, polishing, grinding, attaching). Accordingly, if the micro-tool requires control of an articulated portion thereof, then the present embodiment includes a controller for controlling activation of the micro-tool. Additionally, the present invention may provide coordinated three-dimensional movement of the micro-tool (via the effector) with signals from the controller for performing articulated operations such as threading, orienting a microcomponent/sub assembly within a micromachine being assembled, and/or routing to a particular depth within the base material for the micromachine.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for micromanipulating a biologic material, comprising:

a) positioning a biologic material on a microscope slide;

b) positioning the biologic material on said slide at a desired point beneath a microscope objective, said microscope having a sub-stage capable of rotation about an optical path of said microscope;

c) rotating said sub-stage to a desired orientation;

d) initiating movement of an automatic micromanipulation device to manipulate desired portions of said biologic material;

e) using said micromanipulation device, moving said desired portions of said biologic material to a receptacle; and f) depositing said desired portions of said biologic material into said receptacle;

g) calibrating said automatic micromanipulation device by determining the precise position of a first micro-tool tip and recording information relating to the spatial position of said first micro-tool tip as said micro-tool tip is moved to a desired point beneath a microscope objective, wherein said step of determining comprises positioning said micro-tool tip in the field of view of two CCD cameras and recording a zero position of said micro-tool tip.

2. A method for micromanipulating a biologic material, comprising:

a) positioning a biologic material on a microscope slide;

b) positioning the biologic material on said slide at a desired point beneath a microscope objective, said microscope having a sub-stage capable of rotation about an optical path of said microscope;

c) rotating said sub-stage to a desired orientation;

d) initiating movement of an automatic micromanipulation device to manipulate desired portions of said biologic material;

e) using said micromanipulation device, moving said desired portions of said biologic material to a receptacle; and f) depositing said desired portions of said biologic material into said receptacle;

g) calibrating said automatic micromanipulation device by determining the precise position of a first micro-tool tip and recording information relating to the spatial position of said first micro-tool tip as said micro-tool tip is moved to a desired point beneath a microscope objective, further comprising using said information to coordinate the movement of a second micro-tool to a desired point beneath said microscope objective.

* * * * *